(12) United States Patent
Cinbis

(10) Patent No.: US 8,170,636 B2
(45) Date of Patent: May 1, 2012

(54) OPTICAL SENSOR CONFIDENCE ALGORITHM

(75) Inventor: Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1365 days.

(21) Appl. No.: 11/758,188

(22) Filed: Jun. 5, 2007

(65) Prior Publication Data

US 2008/0306390 A1 Dec. 11, 2008

(51) Int. Cl.
*A61B 5/1455* (2006.01)
*A61B 6/00* (2006.01)

(52) U.S. Cl. ........ 600/310; 600/323; 600/473; 600/476; 600/477

(58) Field of Classification Search .................. 600/310, 600/323, 324, 325, 333, 341; 607/22, 36, 607/122
See application file for complete search history.

(56) References Cited

U.S. PATENT DOCUMENTS

| | | |
|---|---|---|
| 4,202,339 A | 5/1980 | Wirtzfeld |
| 4,257,423 A | 3/1981 | McDonald et al. |
| 4,467,807 A | 8/1984 | Bornzin |
| 4,556,063 A | 12/1985 | Thompson |
| 4,791,935 A | 12/1988 | Baudino et al. |
| 4,821,723 A | 4/1989 | Baker et al. |
| 4,870,968 A | 10/1989 | Wiertzfeld et al. |
| 5,076,271 A | 12/1991 | Lekholm et al. |
| 5,127,404 A | 7/1992 | Wyborny et al. |
| 5,131,388 A | 7/1992 | Pless |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,312,453 A | 5/1994 | Shelton et al. |
| 5,314,430 A | 5/1994 | Bardy |
| 5,330,507 A | 7/1994 | Schwartz |
| 5,331,966 A | 7/1994 | Bennett et al. |
| 5,354,316 A | 10/1994 | Keimel |
| 5,431,172 A | 7/1995 | Hoegnelid et al. |
| 5,545,186 A | 8/1996 | Olson et al. |
| 5,630,413 A * | 5/1997 | Thomas et al. ............... 600/323 |
| 5,902,326 A | 5/1999 | Lessar et al. |
| 6,077,227 A | 6/2000 | Miesel et al. |

(Continued)

FOREIGN PATENT DOCUMENTS

WO    WO0025860 A    5/2000

OTHER PUBLICATIONS

International Search Report, PCT/US2008/065847, Sep. 16, 2008, 5 Pages.

*Primary Examiner* — Eric Winakur
*Assistant Examiner* — Chu Chuan (JJ) Liu
(74) *Attorney, Agent, or Firm* — Michael C. Soldner

(57) ABSTRACT

An implantable medical device system including an optical sensor monitors for the presence of overgrowth on the sensor by sensing light scattered by a measurement volume, the sensed light corresponding to a first wavelength, and deriving an overgrowth metric in response to the sensed light. The overgrowth metric is correlated to the presence of overgrowth on the sensor and is compared to a predetermined threshold. The presence of overgrowth on or near the sensor is detected in response to the overgrowth metric crossing the threshold.

20 Claims, 7 Drawing Sheets

U.S. PATENT DOCUMENTS

| | | |
|---|---|---|
| 6,115,628 A | 9/2000 | Stadler et al. |
| 6,125,290 A | 9/2000 | Miesel |
| 6,128,526 A | 10/2000 | Stadler et al. |
| 6,162,180 A | 12/2000 | Miesel et al. |
| 6,198,952 B1 | 3/2001 | Miesel |
| 6,599,250 B2 | 7/2003 | Webb et al. |
| 6,754,516 B2 * | 6/2004 | Mannheimer ................ 600/323 |
| 6,944,488 B2 | 9/2005 | Roberts |
| 2006/0206019 A1 * | 9/2006 | Zhang et al. ................ 600/323 |
| 2007/0060811 A1 | 3/2007 | Roberts |

* cited by examiner

OPTICAL SENSOR CONFIDENCE ALGORITHM

FIELD OF THE INVENTION

The present invention relates generally to the field of implantable optical sensors and more specifically to a method for detecting erroneous signals due to the presence of overgrowth on or near the optical sensor.

BACKGROUND

Implantable medical devices (IMDs) for monitoring a physiological condition or delivering a therapy typically rely on one or more sensors positioned in a patient's blood vessel, heart chamber, or other portion of the body. Examples of such IMDS include heart monitors, pacemakers, implantable cardioverter-defibrillators (ICDs), myostimulators, nerve stimulators, drug delivery devices, and other IMDs that rely on physiological signals for monitoring a patient and/or controlling a therapy. Implantable sensors used in conjunction with an IMD generally provide a signal related to a physiological condition from which a patient condition or the need for a therapy can be assessed.

As an example, measurement of mixed-venous blood oxygen saturation levels is of interest in determining the metabolic state of the patient. Generally, a decrease in mixed-venous blood oxygen saturation is associated with an increase in physical activity or may reflect insufficient cardiac output or respiratory activity. Thus monitoring mixed-venous blood oxygen saturation allows an implantable medical device to respond to a decrease in oxygen saturation, for example by pacing the heart at a higher rate.

An implantable oxygen sensor for use with an implantable medical device is generally disclosed in commonly assigned U.S. Pat. No. 6,198,952 "Multiple Lens Oxygen Sensor for Medical Electrical Lead" issued to Miesel, hereby incorporated herein by reference in its entirety. Cardiac pacemakers that respond to changes in blood oxygen saturation as measured by an optical sensor are generally disclosed in U.S. Pat. No. 4,202,339 "Cardiac Pacemaker" issued to Wirtzfeld, et al. and in U.S. Pat. No. 4,467,807 "Rate Adaptive Demand Pacemaker" issued to Bornzin, both of which patents are incorporated herein by reference in their entirety. A blood oxygen saturation measurement may also be used to augment arrhythmia detection in a pacemaker/cardioverter/defibrillator (PCD) such as set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" also to Keimel, both incorporated herein by reference in their entireties.

One limitation encountered with the use of implantable optical sensors can arise as the result of thrombus formation over the sensor windows and/or tissue encapsulation of the sensor that occurs as a result of the normal physiological response to a foreign object. Such overgrowth in the form of thrombus formation or tissue encapsulation interferes with the performance of the sensor in accurately measuring blood oxygen or other metabolites. The light reflected back to the sensor may be altered by the overgrowth depending on the optical properties of the overgrowth mass. For example, the light reflected back to the sensor may be increased due to higher reflectance of soft tissue than whole blood. Additionally, the light signal associated with blood oxygen saturation is reduced due to attenuation of emitted light from the optical sensor that reaches the blood volume and attenuation of the reflected light from the blood volume reaching a light detector included in the optical sensor.

The time course and degree of tissue encapsulation of an optical sensor, or any other implanted medical device, is uncertain. Thrombus formation in the vicinity of the sensor due to blood stasis or endothelial injury can occur at unpredictable times after device implant. Because the time course and occurrence of these events is unpredictable, the reliability of physiological measurements using an optical sensor at any point in time may be uncertain.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
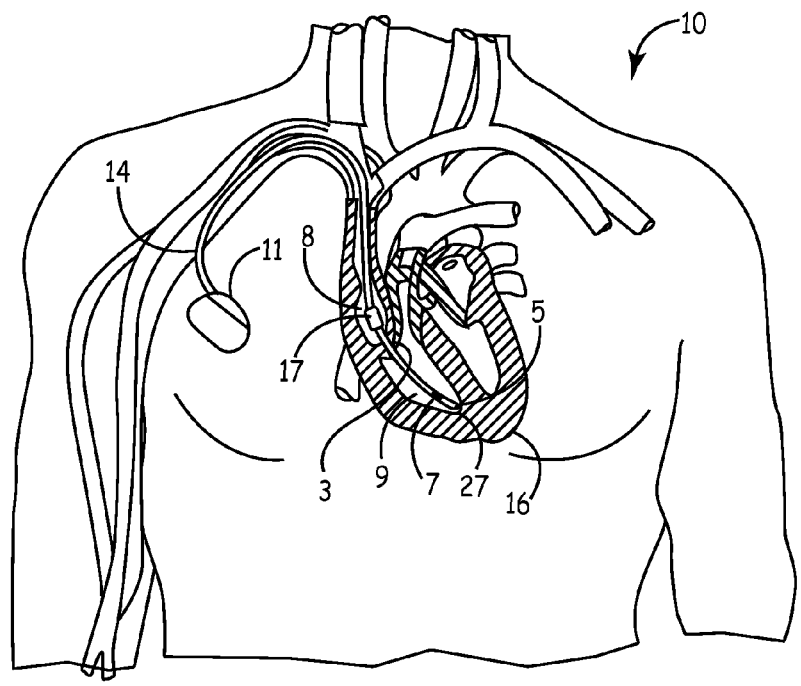
FIG. 1 shows an implantable medical device coupled to an optical sensor implanted in a human body.

In the following description, references are made to illustrative embodiments for carrying out the invention. It is understood that other embodiments may be utilized without departing from the scope of the invention. For purposes of clarity, the same reference numbers are used in the drawings to identify similar elements.

As used herein, the term "overgrowth" refers to any biological tissue or mass on or in the vicinity of an implantable optical sensor obstructing or partially obstructing the normal emission of light from or the detection of light by the sensor. "Overgrowth" includes tissue encapsulating the sensor and formed as a part of the normal foreign body response and thrombus over or near the sensor windows. "Overgrowth" further includes tissue or anatomical structures proximate the sensor that interfere with normal light emission and light measurements from a targeted measurement volume. Shifting or movement of the sensor or a lead carrying the sensor after implantation may dispose the sensor windows near interfering tissue or structures not intended to be included in a targeted measurement volume. "Overgrowth" does not include the blood or tissue volume forming a measurement volume of interest in which light emitted from the sensor is scattered and detected by the sensor for measuring a physiological condition present in the measurement volume.

FIG. 1 shows an implantable medical device (IMD) 11 coupled to an optical sensor 17 that is attached to, or forms part of, lead 14 positioned in heart 16 of patient 10. Lead 14 is attached to IMD 11, shown implanted in the region of the upper right chest of patient 10.

Sensor 17 may be implemented to operate in conjunction with a unipolar, bipolar, or multipolar lead 14 carrying conductors (not shown in FIG. 1), for electrically coupling electrodes and sensors carried by lead 14 to IMD 11. Lead 14 may be employed to operate in cooperation with a wide variety of implantable medical devices. Lead 14 may include a fixation member at its distal end 27 for stabilizing the position of lead 14. Lead 14 is shown to include a tip electrode 5 and a ring electrode 7, used for sensing of electrical signals attendant to the depolarization and repolarization of heart 16, and for transmitting pacing pulses for causing depolarization of cardiac tissue in the vicinity of the electrodes.

IMD 11 may be an implantable cardiac pacemaker, such as of the types disclosed in U.S. Pat. No. 5,158,078 "Rate Responsive Pacemaker and Methods for Optimizing Its Operation" to Bennett et al., U.S. Pat. No. 5,312,453 "Rate Responsive Cardiac Pacemaker and Method for Work-Modulating Pacing Rate Deceleration" to Shelton et al., or U.S. Pat. No. 5,144,949 "Dual Chamber Rate Responsive Pacemaker with Automatic Mode Switching" to Olson, hereby incorporated herein by reference in their respective entireties. IMD 11 may also be a pacemaker-cardioverter-defibrillator (PCD), one embodiment of which is further described below. Embodiments of the present invention may be practiced in conjunction with PCDs, such as those disclosed in U.S. Pat. No. 5,545,186 "Prioritized Rule Based Method and Apparatus for Diagnosis and Treatment of Arrhythmias" to Olson et al., U.S. Pat. No. 5,354,316 "Method and Apparatus for Detection and Treatment of Tachycardia and Fibrillation" to Keimel, U.S. Pat. No. 5,314,430 "Atrial Defibrillator Employing Transvenous and Subcutaneous Electrodes and Method of Use" to Bardy, U.S. Pat. No. 5,131,388 "Implantable Cardiac Defibrillator with Improved Capacitors" to Pless, or U.S. Pat. No. 4,821,723 "Biphasic Waveforms for Defibrillation" to Baker et al., all hereby incorporated herein by reference in their respective entireties. At least some of the devices disclosed in the foregoing patents may be employed in conjunction with optical sensor 17.

Alternatively, IMD 11 may be an implantable nerve stimulator or muscle stimulator, such as those disclosed in U.S. Pat. No. 5,199,428 "Implantable Electrical Nerve Stimulator/Pacemaker with Ischemia for Decreasing Cardiac Workload" to Obel et al., U.S. Pat. No. 5,207,218 "Implantable Pulse Generator" to Carpentier et al., or U.S. Pat. No. 5,330,507 "Implantable Electrical Vagal Stimulation for Prevention or Interruption of Life Threatening Arrhythmias" to Schwartz. The foregoing references are hereby incorporated herein by reference, each in its respective entirety.

In general, IMD 11 shown in FIG. 1 includes a hermetically-sealed housing enclosing circuitry that may include various elements, such as an electrochemical cell (e.g., a lithium battery), circuitry for controlling device operations and recording arrhythmic EGM episodes, a telemetry transceiver antenna and corresponding circuit for receiving data from, and transmitting data to, an external programmer (not shown in FIG. 1).

IMD 11 typically records EGM signals sensed between electrodes 7 and 5 and the output signal provided by optical sensor 17. IMD 11 may be configured to record oxygen saturation data derived from optical sensor signals continuously, periodically at predetermined intervals, or only when a triggering event is sensed, such as disclosed in U.S. Pat. No. 5,331,966 "Subcutaneous Multi-Electrode Sensing System, Method and Pacer" issued to Bennett et al. and incorporated herein by reference in its entirety.

IMD 11 may be embodied as a ventricular pacing pulse generator that operates in a rate responsive, demand pacing mode. IMD 11 may establish a pacing escape interval determined by a rate response algorithm. Such an algorithm typically computes escape intervals on the basis of sensed venous blood oxygen levels as detected using signals generated by sensor 17 and directs delivery of pacing pulses to electrodes 5 and 7, unless R-waves are sensed within the escape interval. A monitoring function may also be incorporated into IMD 11.

Optical sensor 17 may be embodied as an oxygen saturation sensor and is then typically positioned within an area of a living body where flowing venous blood contacts light energy emitted by one or more light emitting diodes (light emitters) disposed within or forming part of sensor 17. Optical sensor 17 may be placed either within a vein that is carrying blood back to heart 16, within right atrium 8 or within right ventricle 9. When embodied as an oxygen saturation sensor, sensor 17 is typically positioned on lead 14 such that sensor 17 is located proximal to ring electrode 7 within right atrium 8 of heart 16. It is generally believed that sensing the oxygen saturation of blood located within right atrium 8 may provide a most sensitive indication of patient exercise levels. Alternatively, sensor 17 may be implanted in the right ventricular outflow tract (RVOT) or pulmonary artery (PA). In alternative embodiments, sensor 17 may be adapted for sensing oxygen saturation of arterial blood and configured for deployment in the left ventricle, left atrium, aorta or peripheral arterial vasculature. When positioned properly within heart 16, lead 14 may be curved or configured such that light emitting and detecting elements of sensor 17 face blood just before it passes through tricuspid valve 3. For a discussion of the manner in which an oxygen sensor may be optimally positioned in right atrium 8 as a control mechanism for a rate responsive pacemaker, see U.S. Pat. No. 5,076,271 "Rate-Responsive Pacing Method and System Employing Minimum Blood Oxygen Saturation as a Control Parameter and as a Physical Activity Indicator" to Lekholm, et al, hereby incorporated by reference herein in its entirety.

In alternative embodiments of the invention, optical sensor 17 may be configured for sensing other metabolite levels, such as glucose levels, or other physiological conditions in a blood or tissue volume of interest. Methods presented herein are described primarily in the context of an optical sensor configured for generating signals correlated to venous oxygen saturation. However, the methods described herein for monitoring for the presence of overgrowth on or in the vicinity of an optical sensor are not limited to the illustrative embodiments of optical oxygen sensors. Rather, the methods described herein and variations thereof may be implemented in conjunction with any implantable optical sensor configured for monitoring a physiological condition in adjacent blood or tissue.

Figure 2:
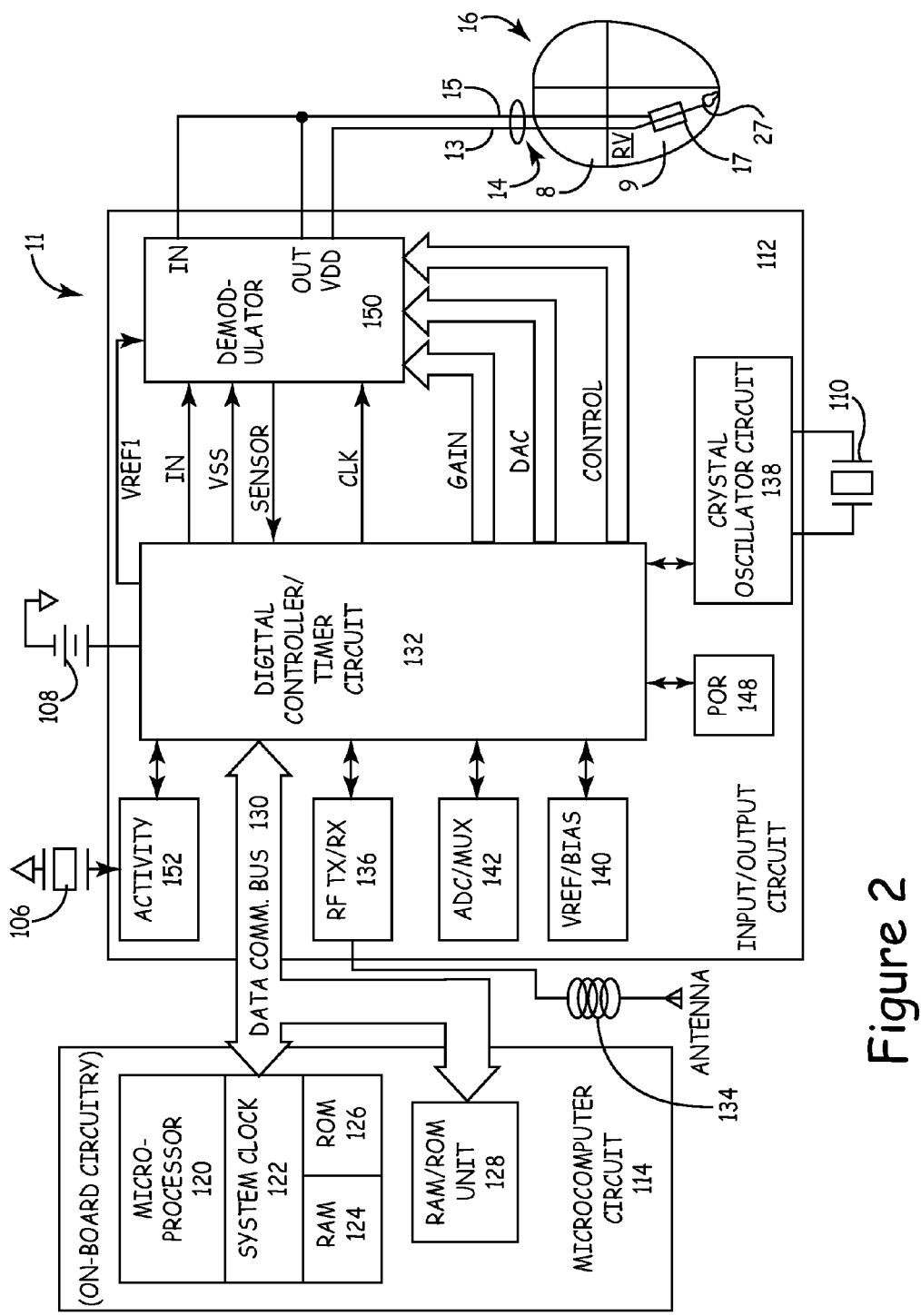
FIG. 2 shows a block diagram of an implantable medical device system including an implantable medical device (IMD) and medical electrical lead carrying an optical sensor for use in sensing blood oxygen saturation.

FIG. 2 shows a block diagram of an IMD and corresponding lead system that derive physiologic information from sensor 17. IMD 11 may be configured as a monitoring only device, or alternatively may be configured for delivering a therapy as part of a pacemaker, PCD, nerve stimulator or the like.

FIG. 2 illustrates patient's heart 16 in relation to lead 14 and sensor 17 in accordance with one embodiment of the present invention. Lead 14 includes first and second lead conductors 13 and 15 extending from sensor 17 disposed near distal end 27.

IMD 11 generally includes input/output circuit 112 coupled to lead conductors 13 and 15, battery 108, optional activity sensor 106, telemetry antenna 134, crystal 110, and microcomputer circuit 114. Input/output circuit 112 includes digital controller/timer circuit 132 and associated components, including crystal oscillator 138, power-on-reset (POR) circuit 148, Vref/BIAS circuit 140, analog-to-digital converter and multiplexer (ADC/MUX) circuit 142, radio frequency transmitter/receiver (RF TX/RX) circuit 136, optional activity circuit 152 and sensor signal demodulator 150.

Crystal oscillator circuit 138 and crystal 110 provide the basic timing clock signals for the digital controller/timer circuit 132. Voltage Reference (Vref)/BIAS circuit 140 generates a stable voltage reference and current levels from battery 108 for the circuits within the digital controller/timer circuit 132, and the other identified circuits including microcomputer circuit 114 and demodulator 150. Power-on-reset circuit 148 responds to initial connection of the circuitry to battery 108 for defining an initial operating condition and also resets the operating condition in response to detection of a low battery voltage condition. Analog-to-digital converter (ADC) and multiplexer circuit 142 digitizes analog sensor signals received by digital controller/timer circuit 132 from demodulator 150 for storage by microcomputer circuit 114.

Data signals transmitted out through RF transmitter/receiver circuit 136 during telemetry are multiplexed by ADC/MUX circuit 142. Voltage reference and bias circuit 140, ADC/MUX circuit 142, POR circuit 148, crystal oscillator circuit 138, and optional activity circuit 152 may correspond to any of those previously described herein or presently used in current marketed, implantable cardiac pacemakers.

Digital controller/timer circuit 132 includes a set of timers and associated logic circuits connected with microcomputer circuit 114 through the data communications bus 130. Microcomputer circuit 114 contains on-board circuits including microprocessor 120, associated system clock 122, and on-board RAM and ROM chips 124 and 126, respectively. In addition, microcomputer circuit 114 includes a separate RAM/ROM chip 128 to provide additional memory capacity. Microprocessor 120 is interrupt driven, operating in a reduced power consumption mode normally, and awakened in response to defined interrupt events, which may include the periodic timing out of data sampling intervals for storage of monitored data, the transfer of triggering and data signals on bus 130, and the receipt of programming signals. A real time clock and calendar function may also be included to correlate stored data to time and date.

Provision may be made for the patient to initiate storage of monitored data through an external programmer or a reed switch closure when an unusual event or symptom is experienced. The monitored data may be related to an event marker and later may be transmitted to an external device for examination by the patient's physician.

Microcomputer circuit 114 controls the operating functions of digital controller/timer 132, specifying which timing intervals are employed, and controlling the duration of the various timing intervals, via bus 130. In alternative embodiments, a control module may employ a digital state machine, ASIC, a combinational logic circuit or the like for controlling device functions in accordance with a programmed operating mode. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. In the embodiment shown, microcomputer circuit 114 operates as a control module employing microprocessor 120. The specific operating modes and timing interval values are programmable. The programmed parameter values and operating modes are received through antenna 134, demodulated in RF transmitter/receiver circuit 136, and stored in RAM 124.

Data transmission to and from an external programmer or monitor (not shown) is accomplished by means of telemetry antenna 134 and the associated RF transmitter and receiver 136, which serves both to demodulate received downlink telemetry and to transmit uplink telemetry. For example, circuitry for demodulating and decoding downlink telemetry may correspond to that disclosed in U.S. Pat. No. 4,556,063 "Telemetry System for a Medical Device" to Thompson and U.S. Pat. No. 4,257,423 "Medical Device" issued to McDonald et al., while uplink telemetry functions may be provided according to U.S. Pat. No. 5,127,404 "Telemetry Format for Implanted Medical Device" issued to Wyborny et al., all which are hereby incorporated by reference herein in their respective entireties. Uplink telemetry capabilities typically include the ability to transmit stored digital information as well as real time physiologic sensor signals, such as EGMs, activity signals, oxygen saturation signals and/or blood pressure signals, for example.

A number of power, timing, and control signals are applied by the digital controller/timer circuit 132 to demodulator 150 to selectively initiate and power the operation of sensor 17, and to selectively read out the applicable signals generated by sensor 17. Monitor 11 periodically stores digitized data related to the various physiologic parameters sensed by the sensor 17 at a nominal sampling frequency which may be related to patient activity level, both optionally correlated to time and date and patient initiated event markers. Depending on the particular configuration of sensor 17, pertinent physiologic parameters, such as parameters relating to patient activity, blood pressure or temperature, blood oxygen or other gas saturation level, and electrogram (EGM) status, may be continuously monitored.

Figure 3:
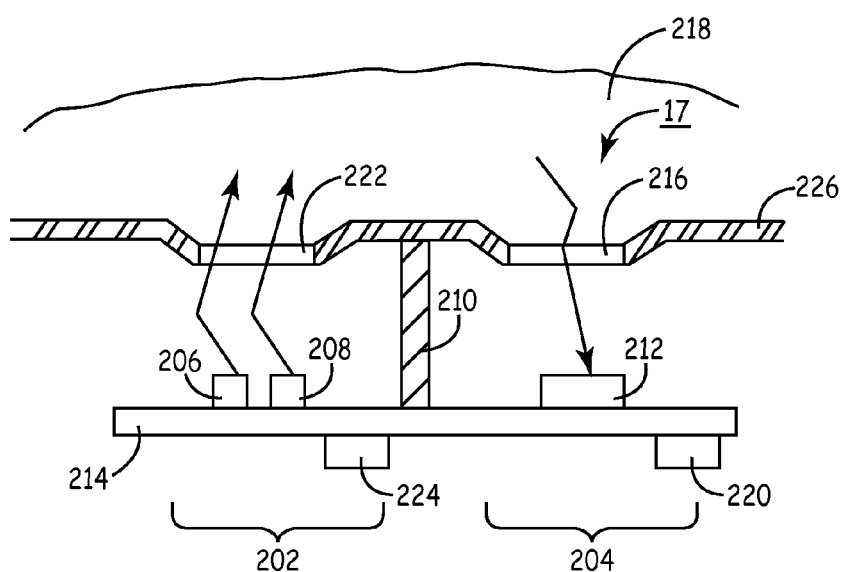
FIG. 3 is a schematic diagram of an optical sensor according to one embodiment of the invention.

An implantable optical sensor for use with an IMD is shown in FIG. 3. Sensor 17 may correspond to the oxygen saturation sensor generally disclosed in the previously-incorporated U.S. Pat. No. 6,198,952 (Miesel). Sensor 17 includes light barrier or baffle 210 disposed between light emitting portion 202 and light detecting portion 204. Light emitting portion 202 may have its own discrete lens 222 separated from lens 216 of light detecting portion 204. Light barrier 210 prevents the direct, reflected or refracted transmission of light that is not scattered by blood volume 218 into light detecting portion 204 for spurious detection by photodetector 212. Lenses 222 and 216 are typically formed of a flat panel, cylinder or half-cylinder of glass, sapphire, ruby, quartz or any other suitable light transparent material.

Light emitting portion 202 includes a light emitter or LED 206 and optionally a second light emitter or LED 208 mounted within a housing 226 of sensor 17. First and second light emitters 206 and 208 sequentially emit light having a first blood oximetry frequency or wavelength and a second blood oximetry frequency or wavelength, respectively. Typically, the second blood oximetry frequency is in the infrared portion of the light spectrum. The first emitted wavelength can be chosen to have an inverse response to a change in oxygen or another measured metabolite concentration as compared to the second emitted wavelength. The inverse response will increase the metabolite-dependent signal when ratiometric algorithms are employed. Light emitters 206 and 208 are mounted on an upper surface of circuit board 214 including integrated circuitry 224 for delivering appropriately-timed driver signals to emitters 206 and 208.

In a two-wavelength optical sensor such as sensor 17 shown in FIG. 3, the amount of scattered light corresponding to one wavelength, e.g. red, is normalized by the amount of scattered light corresponding to a second wavelength, e.g. infrared, to estimate the concentration of a metabolite, e.g. oxygen, present in the measurement volume adjacent the sensor. In an oxygen sensor, red light and infrared light is emitted by the emitting portion 202 and scattered by the measurement volume 218. A portion of the scattered red and infrared light returns to the sensor 17 and is detected by the detecting portion 204. Red light is dependent on oxygen saturation. Infrared light is somewhat less dependent on oxygen saturation than red light and in an inverse relation compared to red light. A time interval is measured for each light wavelength as the time required for the current induced on photodetector 212 integrated over a capacitor to reach a predetermined voltage amplitude. The time interval measured for the red light signal to reach a predetermined voltage amplitude is normalized by the time interval measured for the infrared light signal to account for differences in hematocrit, blood flow velocity and other common-mode signals. The oxygen saturation of the measurement volume 218 is estimated from this ratio of measured red and infrared light.

In alternative embodiments, light emitters 206 and 208 may be pulsed to emit light for predetermined intervals of time during which the current emitted by the photodetector 212 during the intervals of time is integrated to generate a voltage signal proportional to the light intensities. As such, embodiments of the present invention include optical sensors configured to perform time interval based light measurements as well as sensors configured to perform amplitude-based light measurements.

Photodetector 212 sequentially senses the intensity of light originating from light emitters 206 and 208 that is scattered from blood cells in adjacent blood volume 218. Photodetector 212 is mounted on an upper surface of printed circuit board 226, or alternatively a separate circuit board, which includes integrated circuitry 220 for receiving current emitted by photodetector 212 and for transferring an analog or digital signal to signal processing circuitry included in the IMD. In one embodiment of the present invention, integrated circuits 224 and 220 are coupled through lead conductors 13 and 15 of lead 14 to sensor drive circuit and processor circuitry in demodulator 150 as shown in FIG. 2.

Figure 4A:
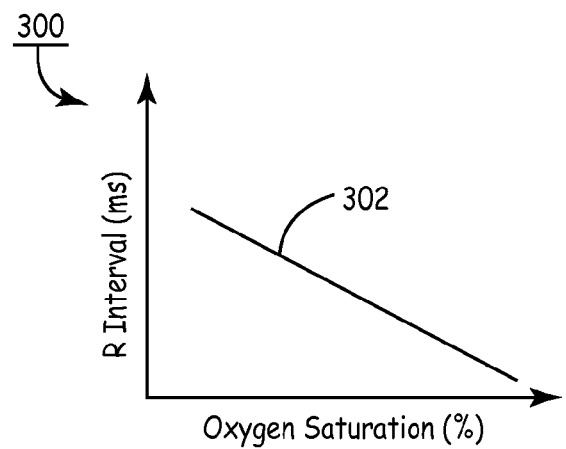
FIG. 4A is a diagram showing the shape of the Red (R) interval response to blood oxygen saturation variation.

FIG. 4A is a graph 300 showing the shape of the Red (R) interval response to blood oxygen saturation variation as might be measured by a time-interval based, optical oxygen sensor. Line 302 represents a decreasing red time interval in ms for increasing oxygen saturation for the illustrative sensor 17 over the range of 20-100% oxygen saturation at 40% blood hematocrit. As oxygen saturation increases, the time interval required for the photodetector current induced by the red light and integrated over a capacitor to reach a predetermined voltage amplitude decreases.

Figure 4B:
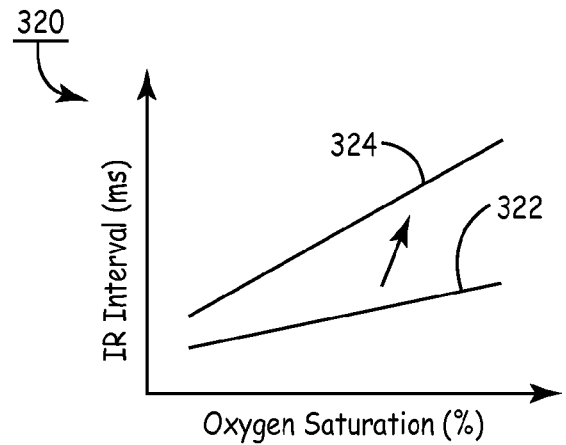
FIG. 4B is a diagram showing the shape of the Infrared (IR) interval response to blood oxygen saturation variation.

FIG. 4B is a graph 320 showing the shape of the Infrared (IR) interval response to blood oxygen saturation variation as might be measured by a time-interval based optical oxygen sensor. Line 322 represents an increasing infrared time interval in ms for increasing oxygen saturation over the range 20-100% oxygen saturation at 40% blood hematocrit. The IR response to oxygen saturation is inversed compared to the R response. Line 324 represents a corrected IR response obtained by multiplying line 322 by a weighting factor (WF).

The weighting factor is selected to generate line 324 having a slope that is inversed compared to the slope of the Red interval response 302 but equal in magnitude.

Figure 4C:
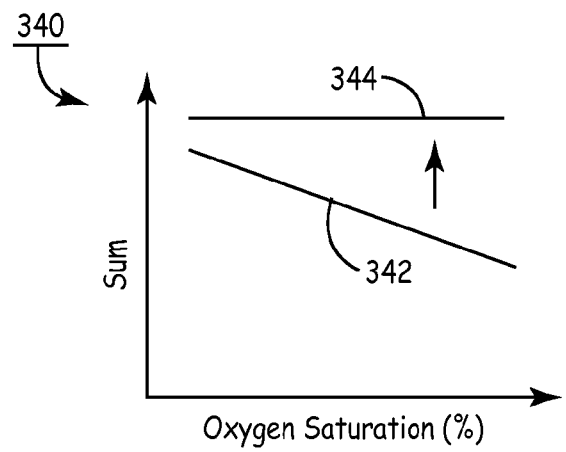
FIG. 4C is a diagram showing the sum of the R and IR interval response to blood oxygen saturation variation.

FIG. 4C is a graph 340 showing the sum of the R and IR interval responses to blood oxygen saturation variation as line 342 over the range of 20-100% oxygen saturation at 40% blood hematocrit. Line 342 represents the sum of line 302, the R interval response, and line 322, the IR interval response, shown in FIGS. 4A and 4B respectively. Line 344 represents the sum of the R interval response (line 302) and corrected IR interval response (line 324 in FIG. 4B). Line 344 can be referred to as the "weighted sum" in that it is the sum of the R interval response and the IR interval response corrected by a weighting factor to produce an oxygen-independent response line 344. The weighted sum can be calculated as:

Weighted sum=($R$ interval)+($WF$)*($IR$ interval).

The baseline weighted sum shown as line 344 represents one estimate of the total R and IR light interval response expected for the sensor independent of blood oxygen saturation. A significant change in the weighted sum computed from measured R and IR intervals after implant using a previously determined weighting factor can be an indication of the presence of overgrowth. The change in the weighted sum may be positive or negative depending on the optical properties of the overgrowth.

For example, fibrotic tissue overgrowth may result in a decrease in absorption and increase in scattering of red and infrared light resulting in a decrease in time interval responses and a decrease in a computed weighted sum. A red thrombus formed over the sensor may result in an increase in absorption of red and infrared light resulting in a large increase in the time interval response and a corresponding increase in the weighted sum. In addition, if the sensor faces cardiac tissue such as myocardium or papillary muscles, both red and IR intervals decrease resulting in a decrease in weighted sum. Accordingly, the weighted sum can be used as a metric correlated to the presence of overgrowth after sensor implantation. This metric can be derived from normal sensor light measurements without additional light sources or detectors. Minimum and maximum thresholds, or an expected functional range, for the weighted sum can determined based on the weighting factor and a baseline weighted sum determined prior to or at implantation.

In order to generate the corrected IR response, various R and IR interval responses are determined at manufacture during a sensor calibration process. During calibration, the slopes of the R and IR interval responses are determined from measured responses over a selected range of oxygen saturation. The weighting factor can be computed as the ratio of the slope of the R interval response to the slope of the IR interval response.

During sensor operation after implantation, a weighted sum is computed using measured R and IR intervals and the previously-determined weighting factor according to the above equation. As will be described in greater detail below, the weighted sum is then compared to a threshold or expected operating range defined based on the baseline weighted sum determined prior to or upon initial implant to detect the presence of overgrowth. In one embodiment, a minimum weighted sum threshold is programmable as percentage, e.g., about 30 to 75% of the baseline weighted sum. A nominal value of the programmable minimum threshold is 67% of the baseline weighted sum. A maximum threshold may be a programmable threshold of a percentage of the baseline weighted sume, e.g. about 125 to 175% of the baseline weighted sum, with a nominal value of 150% of the baseline weighted sum. The weighting factor used for computing the weighted sum may be programmed into the IMD prior to or at the time of implant and stored for use by the IMD in monitoring for sensor overgrowth.

Figure 5A:
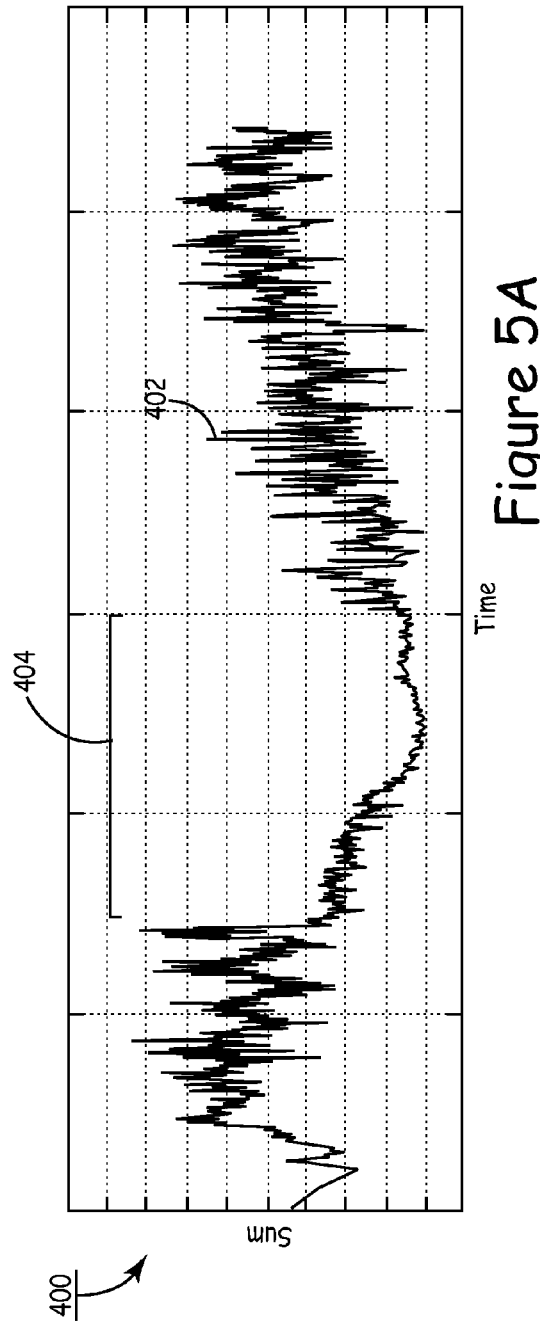
FIG. 5A is a graph of IR interval response as a function of time made from a chronically implanted oxygen sensor.

FIG. 5A is a graph 400 of the IR interval 402 as a function of time made from a chronically implanted oxygen sensor. Due to imperfect mixing of venous blood in the right ventricle and physiologic fluctuations in oxygen saturation, the R and IR intervals are variable. If overgrowth is present, however, the coefficient of variation (CV) of the measured light response will gradually decrease as the amount of the thickness of the encapsulation over the sensor increases or the sensor faces myocardial tissue. This effect is demonstrated by the plotted IR response 402 in FIG. 5A and coefficient of variation plot 422 in FIG. 5B. The section of plot 402 delineated as 404 is approximately a 7-day period of time with a greatly reduced variation of the IR interval.

Figure 5B:
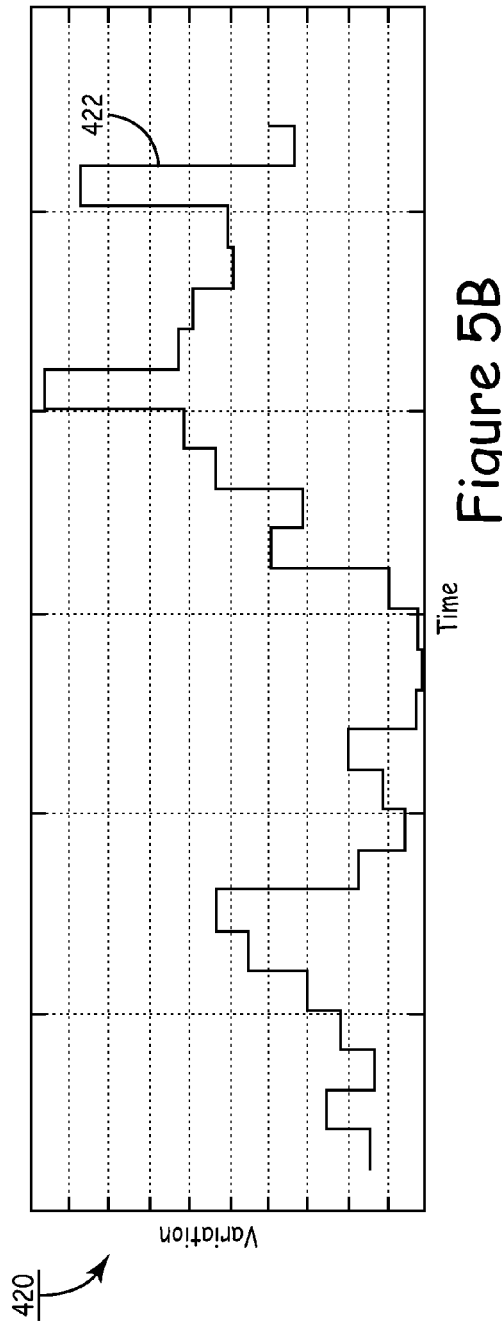
FIG. 5B is a graph of the coefficient of variation of the IR interval response shown in FIG. 5A.

FIG. 5B shows a graph 420 of the CV 422 of the IR interval 402 shown in FIG. 5A computed over daily intervals. Note the reduced CV from approximately day 8 through day 15, which may be due to a thrombus formation or myocardial tissue interference due to lead/sensor shifting. The IMD control module may thus compute the CV, compare it to a programmable threshold and flag sensor data as being affected by suspected overgrowth when the CV declines below a predetermined threshold. In one embodiment, the CV 422 is computed as the standard deviation of all measurements made over a period of time divided by the mean value of the same measurement values. Other computational methods may be used for determining a parameter correlated to the variability of the light measurement. The CV 422 may be computed over any desired interval, e.g. minutes, hours, or days, which may be selected based on individual patient need and the particular physiological parameter being monitored. As will be described below, the CV may be computed for any individual light wavelength response being measured, the weighted sum of two or more monitored light wavelengths, or the physiological parameter, being monitored, such as oxygen saturation.

Figure 6:
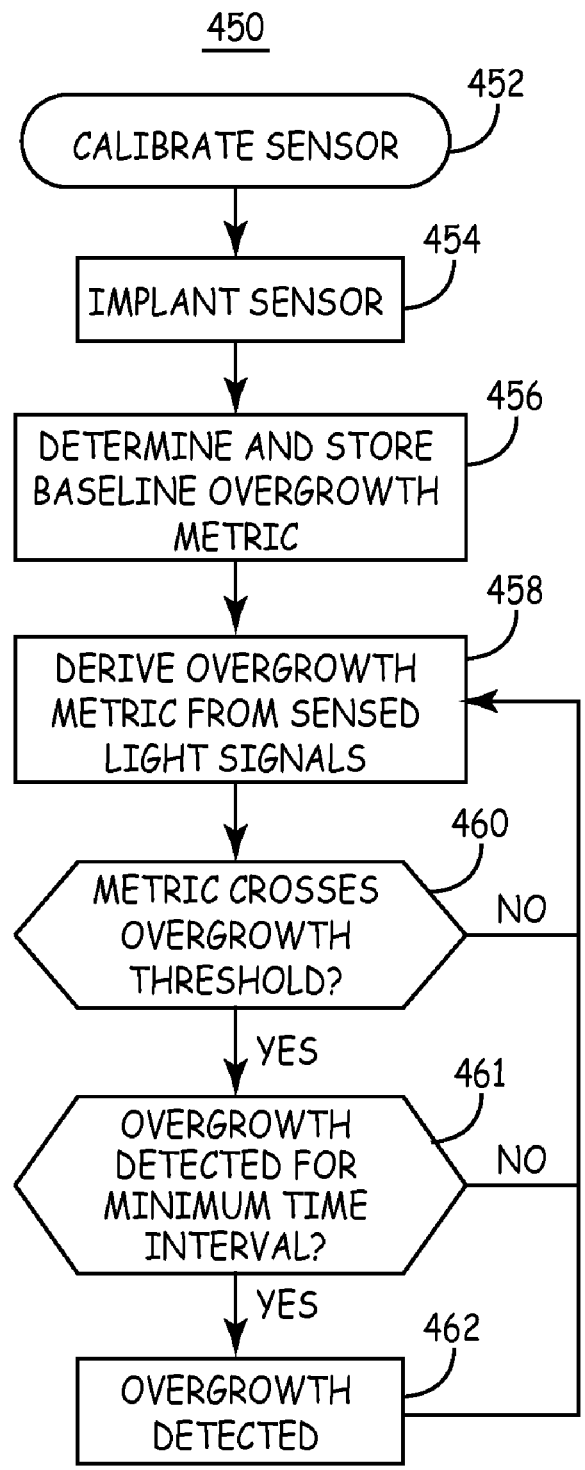
FIG. 6 is a flow chart of a method for monitoring for the presence of overgrowth on or adjacent an optical sensor.

FIG. 6 is a flow chart 450 of a method for monitoring for the presence of overgrowth on or adjacent an optical sensor. Flow chart 450 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the embodiments of the present invention in the context of any modern implantable medical device, given the disclosure herein, is within the abilities of one of skill in the art.

Methods described in conjunction with flow charts presented herein may be implemented, at least in part, in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 452 the sensor is calibrated. Calibration methods may be implemented as generally described in U.S. Pat. No. 6,944,488 to Roberts, incorporated herein by reference in it's entirety. For example, an optical oxygen sensor may be positioned in a simulated blood flow loop to measure the sensor response to varying oxygen saturation conditions. Calibration factors may then be determined to correlate measured R/IR light ratios to known oxygen levels. In some embodiments, a look-up table is generated for each sensor with each entry including an R/IR ratio paired with an oxygen saturation value. In some embodiments, a look-up table containing oxygen saturation values and corresponding R/IR ratios generated during a calibration procedure at the time of manufacture is downlinked to the IMD 11 and stored for use in determining oxygen saturation from measured R/IR ratios. The lookup table may alternatively be stored in an external programmer or monitoring device later uplinked by telemetry from the IMD to a programmer for post processing of the raw R/IR data stored in IMD 11 and uplinked to the programmer along with the look-up table.

At block 454, the sensor is implanted in a patient in conjunction with an IMD system. At block 456, a baseline overgrowth metric is determined at the time of implant, when no overgrowth is known to be present. Alternatively, an overgrowth metric or parameters used in determining an overgrowth metric may be determined previously during the calibration procedure performed at the time of sensor manufacture. Examples of overgrowth metrics include the weighted sum and the CV of a specific light wavelength response, the physiological condition being measured, the weighted sum, or a combination of any of these. As will be described herein, the detection of overgrowth involves deriving an overgrowth metric using light wavelengths normally sensed by the sensor for monitoring a physiologic condition and corresponding to the light wavelengths emitted by the sensor. As such, detection of overgrowth in accordance with the methods described herein does not require any additional light emitting or detecting components.

At block 458, the overgrowth metric is derived from the sensed light signals. The overgrowth metric may be determined on a periodic basis, whenever the sensor is activated to measure a physiological condition or in response to a predetermined change in the measured physiological condition. The derived overgrowth metric is compared to minimum and/or maximum thresholds corresponding to a normal, expected operating range at block 460. If the overgrowth metric crosses an overgrowth detection threshold, the presence of overgrowth is detected at block 462.

In some embodiments, the overgrowth metric may be required to cross the threshold and remain there for a predetermined interval of time, as indicated at decision block 461, prior to detecting overgrowth. The formation of tissue overgrowth is a relatively slow process that may take weeks or months to occur. However a thrombus may form in minutes and be present only temporarily. Thus, the IMD may additionally test the length of time of the perturbation of the overgrowth metric. For example, the IMD may detect overgrowth only after the overgrowth metric crosses a detection threshold for a predetermined time interval. The predetermined time interval may be programmable and be in the range of 1 to 60 minutes. Further more the required total time interval may occur in discontinuous intervals of time. For example, if the overgrowth metric crosses the threshold for n minutes out of the previous m minutes, overgrowth may be detected and corresponding sensor data may be flagged as potentially unreliable. The time interval selected may be tailored to a particular patient and a particular condition being monitored.

The IMD may respond to overgrowth detection by flagging sensor-related data as unreliable, altering control of a therapy normally responsive to changes in the physiological condition monitored by the optical sensor, or generating a patient or physician alert signal. Overgrowth monitoring may continue by returning to block 458 since the presence of overgrowth, such as a thrombus, may be transient and sensor operation may become reliable again at a later time.

Figure 7:
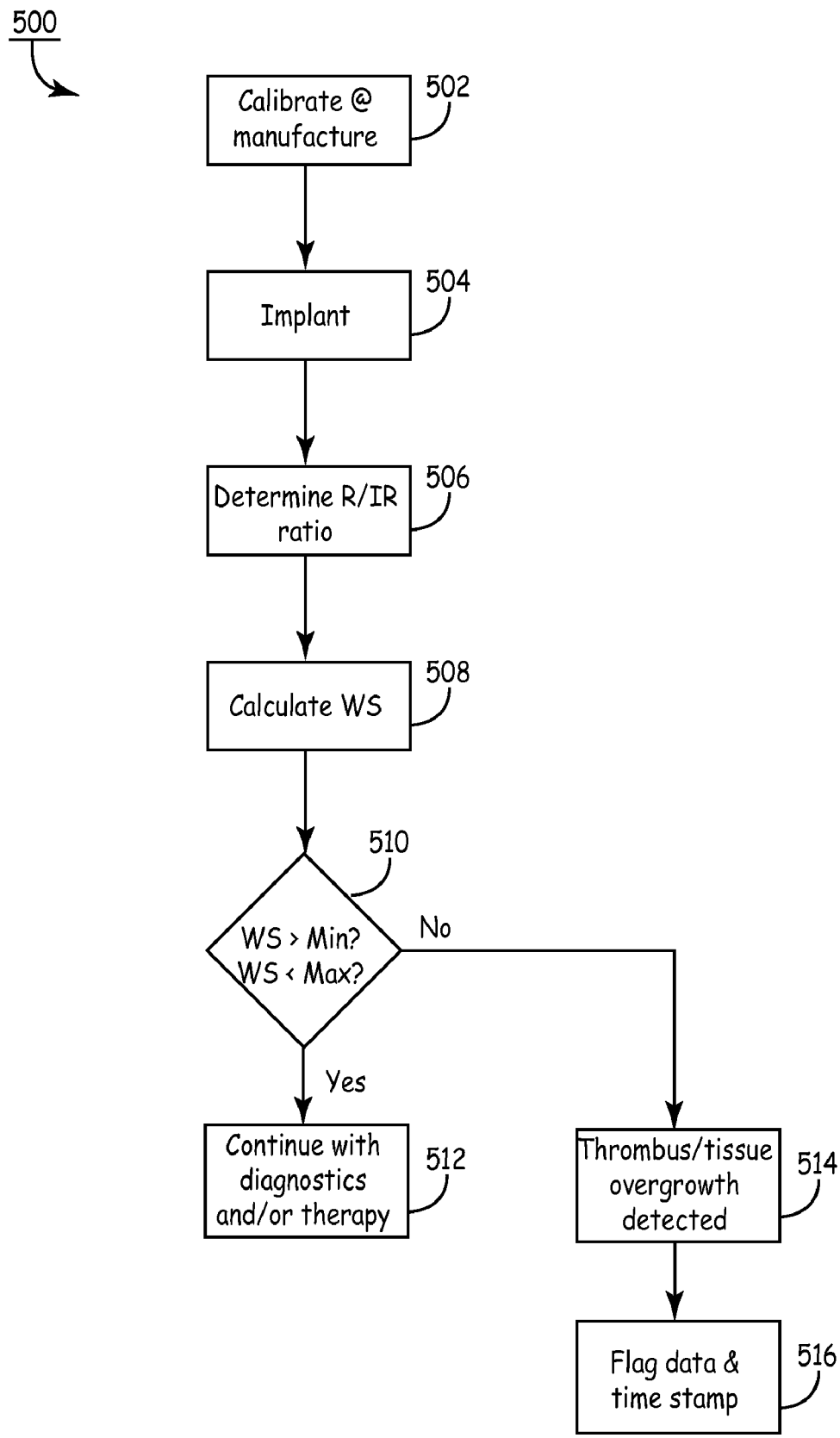
FIG. 7 is a flow chart of a method for estimating blood oxygen saturation and monitoring for the presence of overgrowth.

FIG. 7 is a flow chart 500 of a method for estimating blood oxygen saturation and monitoring for the presence of overgrowth. At block 502, the sensor is calibrated at the time of manufacture as described previously. Calibration factors may be determined to correlate measured R/IR light ratios to known oxygen levels. In some embodiments, a lookup table is generated for each sensor with each entry including an R/IR ratio paired with an oxygen saturation value. The R and IR interval responses over a range of oxygen saturation values is also determined for obtaining the relative slopes of the R and IR interval responses. A unique weighting factor is then computed from the R and IR slopes to match the magnitude of the slope of the IR response to the R response as described previously in conjunction with FIGS. 4A through 4C. The weighting factor and the look-up table or other calibration factors are uplinked to the IMD and stored in IMD memory.

The weighted sum of the R and corrected IR response (using the determined weighting factor) is also computed during calibration 502. This baseline weighted sum will be used for setting a threshold for detecting the presence of overgrowth after implantation. As such, the baseline weighted sum is also uplinked to the IMD and stored in IMD memory.

At block 504, the IMD system including the optical sensor is implanted in a patient. At block 506, the ratio of the sensed R and IR light is measured, using e.g. time-interval based or amplitude-based measurements, for estimating oxygen saturation. The R/IR ratios may be determined on a continuous, periodic or triggered basis as desired an in accordance with a particular monitoring application. Calibration factors or a stored look-up table are used to compute an estimated oxygen saturation from the measured R/IR ratio. When using a look-up table, oxygen saturation for R/IR values falling between stored table values are interpolated between adjacent table entries.

At block 508, a weighted sum is computed by adding the measured R interval to the measured IR interval corrected by the stored weighting factor. The new weighted sum value found at block 508 is compared to a programmable minimum threshold, e.g., 30 to 75% of the baseline weighted sum, and a programmable maximum threshold, e.g., 125-175% of the baseline weighted sum, at block 510. If the answer at block 510 is yes, no overgrowth is detected, and the IMD 11 continues processing diagnostics and/or controlling therapy delivery using the valid oxygen saturation data.

If, however, the new weighted sum falls outside the predefined operating range as determined at block 510, overgrowth is detected at block 514. At block 516, any oxygen saturation data based on the R and IR measurements found to be associated with an out of range weighted sum value is flagged as being potentially erroneous due to overgrowth. Typically, the oxygen saturation data and overgrowth detection indicator is stored in memory (RAM memory 124 FIG. 2) and a time stamp is provided to allow subsequent uplink and review of the information by the patient's physician.

Figure 8:
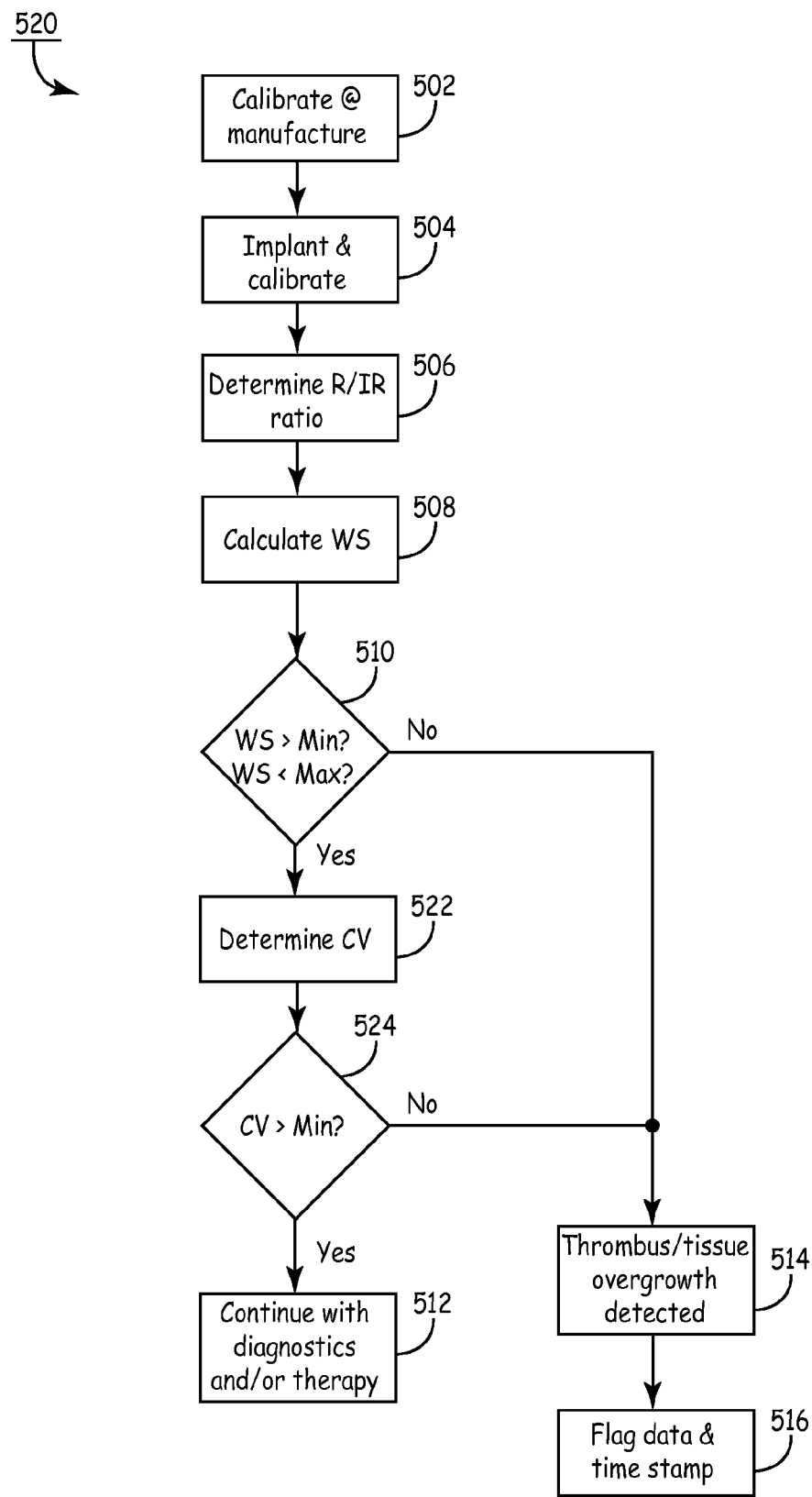
FIG. 8 is a flow chart of an alternative method for estimating blood oxygen saturation and monitoring for overgrowth.

FIG. 8 is a flow diagram 520 of an alternative method for estimating blood oxygen saturation and monitoring for overgrowth. Similar to the flow diagram of FIG. 7, at block 502, a calibration procedure is performed to generate calibration factors for use in estimating oxygen saturation. In one embodiment, a look-up table is generated with each entry including an R/IR ratio paired with an oxygen saturation value. A unique weighting factor is also determined to match the slope of IR response to R response and for determining a baseline weighted sum of the R and corrected IR responses which is independent of oxygen saturation variation. The weighting factor and the baseline weighted sum will be stored in memory of the IMD.

At block 504, the IMD system including the calibrated optical sensor is implanted in a patient and the sensor specific lookup table is downloaded into the IMD via telemetry. Additionally at block 504, a blood sample may be drawn from the patient and analyzed in a blood gas analyzer. Any difference between a sensor-measured oxygen saturation and the oxygen saturation measured by the blood gas analyzer can be used as an additional calibration factor to correct for any offset between the sensor and blood gas analyzer oxygen saturation measurements. A programmer can be used to initiate a calibration period (for example, 1 minute or a fixed number of samples, e.g., 60 samples) to determine nominal sensor function in terms of signal variability. A standard deviation and mean of the R, IR, estimated oxygen, or weighted sum can be computed from the measurements obtained over the calibration period for use in computing a baseline CV.

At block 506, the R/IR ratio is determined from measured light responses. An oxygen saturation estimate is made from the measured R/IR ratio using stored calibration factors or a stored look-up table. Ratio values falling between table values are interpolated between adjacent table entries as needed. At block 508, the weighted sum is computed by adding the R interval response to the IR interval response corrected by the previously determined weighting factor. The weighted sum value found at block 508 is compared to a programmable minimum threshold and a programmable maximum threshold at block 510, as described herein above. If the answer at block 510 is Yes, a coefficient of variability (CV) is determined at block 522. Note that either the measured R, IR, oxygen saturation, and/or computed WS value may be used for the CV evaluation.

At block 524 the CV value(s) found at block 522 is compared to a programmable minimum threshold. A minimum threshold may be defined as a percentage of a baseline CV, e.g., 10-75% of the baseline CV, as a change relative to a previous interval of time, or as a nominally selected CV. If the answer at block 524 is Yes, the IMD continues processing diagnostics and/or controlling therapy delivery according to programmed operating modes using the valid oxygen saturation data at block 512.

If, however, the CV is less than an overgrowth detection threshold as determined at block 524, overgrowth is detected at block 514. At block 516, the oxygen saturation data is flagged as being potentially erroneous due to the detected presence of overgrowth. Typically, the data is stored in memory (RAM memory 124 FIG. 2) and a time stamp is provided to allow subsequent uplink and review of information by the patient's physician. While both a test involving the weighted sum and the CV is used in method 520 for detecting overgrowth presence, it is recognized that either the weighted sum or a CV parameter may be used alone, simultaneously, or sequentially for detecting overgrowth.

It is further recognized that the methods 500 and 520 shown in FIG. 7 and 8 may include measuring the length of time either, or both, a WS (at block 510) and CV (at block 524) parameter cross an overgrowth detection threshold. For example, criteria for overgrowth detection may require that an overgrowth metric cross a detection threshold and remain there for a programmable continuous or discontinuous interval of time, e.g., 5-60 minutes, before detecting overgrowth. Thus, an implantable optical sensor and associated method for detecting the presence of overgrowth have been described herein. It will be apparent from the foregoing that while particular embodiments of the invention have been illustrated and described, various modifications can be made without departing from the spirit and scope of the invention. Accordingly, it is not intended that the invention be limited, except as by the appended claims.

The invention claimed is:

1. A method for use with an implantable optical sensor, comprising:
   emitting light from a light emitting portion of the optical sensor;
   sensing light emitted through a lens of the emitting portion and scattered by a measurement volume through a lens of a light detecting portion of the optical sensor, the sensed light corresponding to a first wavelength, the light emitting portion and the light detecting portion separated by a light barrier;
   deriving a metric in response to the sensed light, the metric correlated to the presence of overgrowth on the sensor;
   comparing the metric to a predetermined threshold; and
   determining the presence of overgrowth on the sensor in response to the comparing.

2. The method of claim 1 wherein deriving the metric comprises determining a first parameter correlated to the intensity of the sensed light.

3. The method of claim 2 wherein the intensity of the sensed light corresponding to the first wavelength is modulated by a physiological condition and wherein deriving the metric further comprises determining a weighting factor corresponding to an intensity of the sensed light that is independent of the physiological condition.

4. The method of claim 3 further comprising sensing light scattered by the measurement volume corresponding to a second wavelength, the intensity of the sensed light corresponding to the second wavelength being modulated by the physiological condition, and
   wherein deriving the metric further comprises determining a second parameter correlated to the intensity of the sensed light corresponding to the second wavelength, and determining a weighted sum of the first parameter and the second parameter.

5. The method of claim 4 wherein deriving the metric further comprises determining a variability of the weighted sum.

6. The method of claim 2 wherein deriving the metric further comprises determining a variability of the first parameter.

7. The method of claim 2 further comprising determining a physiological condition in response to the determined first parameter and wherein deriving the metric further comprises determining a variability of the physiological condition.

8. The method of claim 1 further comprising:
   storing data corresponding to the sensed light; and
   marking stored data in response to determining the presence of overgrowth on the sensor.

9. The method of claim 1 wherein determining the presence of overgrowth comprises determining the metric crosses the threshold for a predetermined interval of time.

10. The method of claim 1, further comprising:
    measuring a first slope of a response of the first wavelength to varying oxygen saturation in a measurement volume and a second slope of a response of a second wavelength to varying oxygen saturation in a measurement volume;
    computing a weighting factor as a ratio of the first slope and the second slope;
    measuring a first light wavelength signal and a second light wavelength signal correlated to light scattered by the measurement volume into the light detecting portion of the optical sensor; and
    deriving the metric as a weighted sum of the measured first light wavelength signal and a product of the weighting factor and the measured second light wavelength signal.

11. A non-transitory computer readable medium for storing a set of instructions which when implemented in an implantable medical device system including an optical sensor cause the system to:
    emit light from a light emitting portion of the optical sensor;
    sense light emitted through a lens of the emitting portion and scattered by a measurement volume through a lens of a light detecting portion of the optical sensor and corresponding to a first wavelength, the light emitting portion and the light detecting portion separated by a light barrier;
    derive a metric in response to the sensed light, the metric correlated to the presence of overgrowth on the sensor;
    compare the metric to a predetermined threshold; and
    determine the presence of overgrowth on the sensor in response to the comparing.

12. An implantable medical device, comprising:
    an optical sensor comprising an emitting portion and a detecting portion separated by an light barrier and configured to sense light emitted through a lens of the emitting portion and scattered by a measurement volume through a lens of the detecting portion, the light corresponding to a first wavelength;
    a control module configured to receive a signal from the optical sensor corresponding to the sensed light, derive a metric in response to the received signal, the metric correlated to the presence of overgrowth on the sensor, compare the metric to a predetermined threshold; and determine the presence of overgrowth on the sensor in response to the comparing.

13. The device of claim 12 wherein deriving the metric comprises determining a first parameter correlated to the intensity of the sensed light.

14. The device of claim 13 wherein the intensity of the sensed light corresponding to the first wavelength is modulated by a physiological condition and wherein deriving the metric further comprises determining a weighting factor corresponding to an intensity of the sensed light that is independent of the physiological condition.

15. The device of claim 14 wherein the optical sensor further configured to sense light scattered by the measurement volume corresponding to a second wavelength, the intensity of the sensed light corresponding to the second wavelength being modulated by the physiological condition,
    wherein deriving the metric further comprises determining a second parameter correlated to the intensity of the sensed light corresponding to the second wavelength and determining a weighted sum of the first parameter and the second parameter.

16. The device of claim 15 wherein deriving the metric further comprises determining a variability of the weighted sum.

17. The device of claim 13 wherein deriving the metric further comprises determining a variability of the first parameter.

18. The device of claim 13 wherein the control module is further configured to determine a physiological condition in response to the determined first parameter and wherein deriving the metric further comprises determining a variability of the physiological condition.

19. The device of claim 12 further comprising:
a memory for storing data corresponding to the sensed light,
wherein the control module further configured to mark stored data in response to determining the presence of overgrowth on the sensor.

20. The device of claim 12 wherein determining the presence of overgrowth comprises determining the metric crosses the threshold for a predetermined interval of time.

* * * * *